United States Patent [19]

Wieringa et al.

[11] Patent Number: 5,258,392

[45] Date of Patent: Nov. 2, 1993

[54] 3-QUINUCLIDINE DERIVATIVES

[75] Inventors: Johannes H. Wieringa, Heesch; Sjoerd F. van Aelst, Megen; Ralf Plate, Oss, all of Netherlands

[73] Assignee: Akzo N.V., Arnhem, Netherlands

[21] Appl. No.: 830,107

[22] Filed: Jan. 31, 1992

[30] Foreign Application Priority Data

Feb. 1, 1991 [EP] European Pat. Off. ........ 91200196.3

[51] Int. Cl.$^5$ .................. A61K 31/445; C07D 453/02
[52] U.S. Cl. .................... 514/305; 514/879; 546/137
[58] Field of Search ................. 546/137; 514/305, 879

[56] References Cited

U.S. PATENT DOCUMENTS

| | | | |
|---|---|---|---|
| 2,901,486 | 8/1959 | Grob | 546/137 X |
| 3,405,134 | 10/1968 | Judd | 547/137 |
| 3,796,714 | 3/1974 | Brack | 546/137 X |
| 3,821,248 | 6/1974 | Griot | 546/137 X |
| 4,531,967 | 7/1985 | Van Heertum | 546/137 X |
| 4,593,034 | 6/1986 | Munson et al. | 514/305 |
| 4,599,344 | 7/1986 | Morgan, Jr. | 546/137 X |
| 4,605,652 | 8/1986 | Welstead et al. | 514/214 |
| 4,843,074 | 6/1989 | Rzeszotarski | 546/137 X |
| 4,853,376 | 8/1989 | King | 514/161 |
| 4,921,860 | 5/1990 | Cliffe | 514/304 |

FOREIGN PATENT DOCUMENTS 0311724 4/1989 European Pat. Off. .

Primary Examiner—Marianne M. Cintins
Assistant Examiner—Catherine Scalzo
Attorney, Agent, or Firm—Donna Bobrowicz

[57] ABSTRACT

The invention relates to a 3-quinuclidine derivative having the formula I

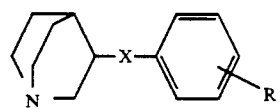

wherein X is O or S, and R represents one to five substituents independently selected from hydrogen, hydroxy, lower alkyl, lower alkoxy, lower aralkyloxy, lower alkanoyloxy, halogen, $NO_2$, $CF_3$, CN, $NR_1R_2$, and $COR_3$, in which $R_1$ and $R_2$ are independently selected from hydrogen, lower alkyl, and lower alkanoyl, and $R_3$ is selected from OH, lower alkyl, lower alkoxy, and $NR_4R_5$, wherein $R_4$ and $R_5$ are independently hydrogen or lower alkyl; or pharmaceutically acceptable salts thereof.

9 Claims, No Drawings

3-QUINUCLIDINE DERIVATIVES

The invention relates to 3-quinuclidine derivatives, a process for the preparation thereof, a pharmaceutical composition containing the same, as well as to the use of these 3-quinuclidine derivatives for the preparation of a medicament.

Related quinuclidine derivatives are known, for instance (2-quinuclidinyl)-phenylether which is disclosed by C. A. Grob and A. Sieber in Helv. Chim. Acta 50 (8), 2531–42 (1967). This compound was obtained by fragmentation of (2-quinuclidinyl)-phenylketoxime tosylate, however, no pharmacological activity was assessed or suggested.

The present invention relates to a 3-quinuclidine derivative having the formula I

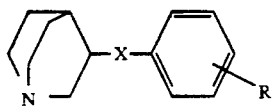

wherein X is O or S, and R represents one to five substituents independently selected from hydrogen, hydroxy, lower alkyl, lower alkoxy, lower aralkyloxy, lower alkanoyloxy, halogen, $NO_2$, $CF_3$, CN, $NR_1R_2$, and $COR_3$, in which $R_1$ and $R_2$ are independently selected from hydrogen, lower alkyl, and lower alkanoyl, and $R_3$ is selected from OH, lower alkyl, lower alkoxy, and $NR_4R_5$, wherein $R_4$ and $R_5$ are independently hydrogen or lower alkyl; or pharmaceutically acceptable salts thereof.

The compounds of this invention have muscarinic properties. They bind to muscarinic agonist receptor sites with a 2 to 750 fold preference as compared to muscarinic antagonist receptor sites, as is exemplified in their ability to bind preferentially to the agonist site of muscarinic receptors in membrane preparations of rat cerebral cortex, or membrane from rat forebrain. Preferred compounds show an agonist/antagonist binding ratio of between 10 and 400. Compounds having ratios very much higher than 750 are undesired, because they may exert side-effects or toxic properties. Compounds having similar pharmacological properties are known, e.g. pilocarpine and oxotremorine, but the chemical structures of these compounds bear no relation to the 3-quinuclidine derivatives of this invention. The 3-quinuclidine derivatives are suitable for the treatment of cognition disorders, like presenile and senile dementia, including Alzheimer's disease, and for the treatment of other cholinergic deficiencies, like Huntington's chorea, tardive dyskinesia, hyperkinesia, mania, and Tourette syndrome.

Preferred compounds according to the invention are the 3-quinuclidine derivatives in which X is O, and more preferably 3-quinuclidine derivatives in which X is O and R is selected from $CF_3$, bromine, or iodine. Preferably R represents one substituent in the ortho position.

The term halogen used in the definition of formula I means fluorine, chlorine, bromine, or iodine. Bromine and iodine are preferred halogens.

The term lower alkyl means a branched or unbranched alkyl group with 1–4 carbon atoms, such as methyl, ethyl, propyl, isopropyl, butyl, or tert-butyl.

The alkyl moiety which is present in the lower alkoxy group has the same meaning as previously defined for lower alkyl.

The term lower alkanoyl means an alkanoyl (acyl) group, the alkyl moiety of which has the same meaning as lower alkyl. Acetyl is the preferred lower alkanoyl group. The alkanoyl group in the lower alkanoyloxy group has the same meaning.

The term lower aralkyloxy means an aralkyloxy group, the alkyl moiety of which has 1–4 carbon atoms, and preferably is a methylene group, and the aryl moiety of which is preferably a phenyl group, optionally substituted with hydroxy, lower alkyl, lower alkoxy, or halogen. The preferred aralkyloxy group is the phenylmethoxy (benzyloxy) group.

The novel compounds of formula I may be isolated from the reaction mixture in the form of a pharmaceutically acceptable salt. The pharmaceutically acceptable salts may also be obtained by treating the free base of formula I with an organic or inorganic acid such as HCl, HBr, HI, $H_2SO_4$, $H_3PO_4$, acetic acid, propionic acid, glycolic acid, maleic acid, malonic acid, methanesulphonic acid, fumaric acid, succinic acid, tartaric acid, citric acid, benzoic acid, and ascorbic acid.

The compounds of this invention possess a chiral carbon atom, and may therefore be obtained as a pure enantiomer, or as a mixture of enantiomers, among which the racemic mixture. Methods for obtaining the pure enantiomers are well known in the art, e.g. synthesis from chirally pure 3-quinuclidinol or 3-thioquinuclidinol, crystallization of salts which are obtained from optically active acids and the racemic mixture, or chromatography using chiral columns.

The 3-quinuclidine derivatives of the invention can be prepared by methods known for the preparation of analogous compounds.

A suitable method is the condensation of 3-quinuclidinol or 3-thioquinuclidinol with a benzene derivative having the formula II

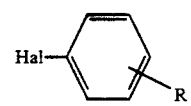

wherein R has the previously given meaning and Hal is a halogen (fluorine, chlorine, bromine, or iodine), or with a iodonium derivative having the formula III

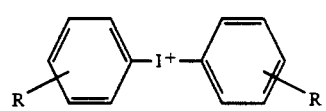

wherein R has the previously given meaning, after which the compound obtained may be separated into its enantiomers and/or may be converted into a pharmaceutically acceptable salt.

It is possible to convert the products obtained by the previously mentioned procedure into another product according to the invention. Using generally known methods it is, for instance, possible to convert aromatic substituents into other aromatic substituents. Alkoxy substituents may be treated with strong acids such as $BBr_3$, to give the hydroxy substituent. Hydroxy substituted compounds may be condensed with lower alcohols in acidic medium to give alkoxy derivatives, or may be acylated with acyl anhydrides to give alkanoyl substituted derivatives, and nitro substituted compounds may be reduced to afford amine compounds. Compounds wherein $R_1$, $R_2$, $R_3$ and/or $R_4$ are hydrogen may be alkylated, e.g. by a Leuckart-Wallach reaction, to afford compounds wherein $R_1$, $R_2$, $R_3$ and/or $R_4$ are alkyl. This is further exemplified in the examples.

The compounds of the invention may be administered enterally or parenterally, and for humans preferably in a daily dosage of 0.001–10 mg per kg body weight. Mixed with pharmaceutically suitable auxiliaries, e.g. as described in the standard reference, Chase et al., Remington's Pharmaceutical Sciences, the compounds may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. a nasal spray.

The invention is further illustrated by the following examples.

EXAMPLE 1

3-[2-(trifluoromethyl)phenoxy]-1-azabicyclo[2.2.2]octane ethanedioate

A solution of 1.78 g (14 mmol) of 3-quinuclidinol in 20 ml of dry N,N-dimethylformamide (DMF) was added dropwise under nitrogen to a suspension of 0.6 g (15 mmol) of sodium hydride in 20 ml of dry DMF. The mixture was stirred for 15 min at 70° C., and a solution of 3.8 ml (30 mmol) of 2-fluoro-(trifluoromethyl)benzene in 8 ml of dry DMF was added dropwise. The mixture was stirred for another 1.5 h, after which the solvent was evaporated. The residue was dissolved in ethyl acetate and washed with brine. The ethyl acetate layer was separated, dried over magnesium sulfate and evaporated to dryness. The crude compound was purified by column chromatography on silica using methanol-dichloromethane (2:8) as eluent to give 3.0 g (59% yield) of 3-[2-(trifluoromethyl)phenoxy]-1-azabicyclo[2.2.2 ]octane, which was converted into the oxalate salt by treatment with oxalic acid and recrystallization from methanol. m.p. 174° C.

EXAMPLE 2

In an analogous manner as described in Example 1 were prepared:

3-phenoxy-1-azabicyclo[2.2.2]octane. m.p. 49° C.
3-(4-nitrophenoxy)-1-azabicyclo[2.2.2]octane hydrochloride. m.p. 242° C.
3-(3-nitrophenoxy)-1-azabicyclo[2.2.2]octane hydrochloride. m.p. 230° C.
3-(2-nitrophenoxy)-1-azabicyclo[2.2.2]octane hydrochloride. m.p. 237° C.
3-[3-(trifluoromethyl)phenoxy]-1-azabicyclo[2.2.2]octane hydrochloride. m.p. 206° C.
3-[4-(trifluoromethyl)phenoxy]-1-azabicyclo[2.2.2]octane hydrochloride. m.p. 181° C.
3-(2-chlorophenoxy)-1-azabicyclo[2.2.2]octane hydrochloride. m.p. 184° C.
3-(3-chlorophenoxy)-1-azabicyclo[2.2.2]octane hydrochloride. m.p. 196° C.
3-(4-chlorophenoxy)-1-azabicyclo[2.2.2]octane. m. p. 66° C.
3-(4-chlorophenoxy)-1-azabicyclo[2.2.2]octane hydrochloride. m.p. 198° C.
3-(3,4-dichlorophenoxy)-1-azabicyclo[2.2.2]octane (Z)-2-butenedioate. m.p. 129° C.
3-(2,6-dichlorophenoxy)-1-azabicyclo[2.2.2]octane (Z)-2-butenedioate. m.p. 137° C.
3-(2,3-dichlorophenoxy)-1-azabicyclo[2.2.2]octane (Z)-2-butenedioate. m.p. 179° C.
3-(2,4-dichlorophenoxy)-1-azabicyclo[2.2.2]octane (Z)-2-butenedioate. m.p. 154° C.
3-(3-fluorophenoxy)-1-azabicyclo[2.2.2]octane hydrochloride. m.p. 206° C.
3-(2-fluorophenoxy)-1-azabicyclo[2.2.2]octane (Z)-2-butenedioate. m.p. 92° C.
3-(2-fluorophenoxy)-1-azabicyclo[2.2.2]octane ethanedioate. m.p. 174° C.
3-(2-bromophenoxy)-1-azabicyclo[2.2.2]octane (Z)-2-butenedioate. m.p. 139° C.
3-(2-iodophenoxy)-1-azabicyclo[2.2.2]octane (Z)-2-butenedioate. m.p. 159° C.
3-(4-methoxyphenoxy)-1-azabicyclo[2.2.2]octane (oil).
3-(3-methoxyphenoxy)-1-azabicyclo[2.2.2]octane (oil).
3-(2-methoxyphenoxy)-1-azabicyclo[2.2.2]octane hydrochloride. m.p. 166° C.
3-[2-(phenylmethoxy)phenoxy]-1-azabicyclo[2.2.2]octane (oil).
2-[(1-azabicyclo[2.2.2]oct-3-yl)oxy]phenol (Z)-2-butenedioate (obtained by catalytic hydrogenation of 3-[2-(phenylmethoxy)phenoxy]-1-azabicyclo[2.2.2]-octane). m.p. 126° C.
2-[(1-azabicyclo[2.2.2]oct-3-yl)oxy]phenol acetate (Z)-2-butenedioate (obtained by acetanhydride/$K_2CO_3$ treatment of 2-[(1-azabicyclo[2.2.2]oct-3-yl)oxy]phenol). m.p. 161° C.
2-[(1-azabicyclo[2.2.2]oct-3-yl)oxy]benzenamine dihydrochloride (obtained by catalytic hydrogenation of 3-(2-nitrophenoxy)-1-azabicyclo[2.2.2]octane). m.p. >250° C.
3-[(1-azabicyclo[2.2.2]oct-3-yl)oxy]benzenamine dihydrochloride (obtained by catalytic hydrogenation of 3-(3-nitrophenoxy)-1-azabicyclo[2.2.2]octane).
4-[(1-azabicyclo[2.2.2]oct-3-yl)oxy]benzenamine dihydrochloride (obtained by catalytic hydrogenation of 3-(4-nitrophenoxy)-1-azabicyclo[2.2.2]octane). m.p. >250° C.
N-[4-(1-azabicyclo[2.2.2]oct-3-yl)oxy]phenyl]acetamide hydrochloride (obtained by acetylation of 4-[(1-azabicyclo[2.2.2]oct-3-yl)oxy]benzenamine). m.p. >250° C.
2-[(1-azabicyclo[2.2.2]oct-3-yl)oxy]benzonitrile (Z)-2-butenedioate. m.p. 137° C.
3-[(1-azabicyclo[2.2.2]oct-3-yl)oxy]benzonitrile (Z)-2-butenedioate.
4-[(1-azabicyclo[2.2.2]oct-3-yl)oxy]benzonitrile (Z)-2-butenedioate. 2-[(1-azabicyclo[2.2.2]oct-3-yl)oxy]-benzenecarboxamide (obtained by KOH/t-butanol hydrolysis of 2-[(1-azabicyclo[2.2.2]oct-3-yl)oxy]benzonitrile). m.p. 144° C.
4-[(1-azabicyclo[2.2.2]oct-3-yl)oxy]benzencarboxamide hydrochloride. m.p. >250° C.
3-[(1-azabicyclo[2.2.2]oct-3-yl)oxy]benzenecarboxamide hydrochloride. m.p. >250° C.
2-[(1-azabicyclo[2.2.2]oct-3-yl)oxy]benzoic acid.

EXAMPLE 3

4-[(1-azabicyclo[2.2.2]oct-3-yl)oxy]benzenamine dihydrochloride 3-(4-nitrophenoxy)-1-azabicyclo[2.2.2]octane (Example 2) was submitted to catalytic hydrogenation with Pd/C in ethanol, after which the free base was converted into the hydrochloric salt to obtain 4-[(1-azabicyclo[2.2.2]-oct-3-yl)oxy]benzenamine dihydrochloride. M.p. >250° C.

EXAMPLE 4

N-[4-[(1azabicyclo[2.2.2]oct-3-yl)oxy]phenyl]acetamide hydrochloride

4-[(1-azabicyclo[2.2.2]oct-3-yl)oxy]benzenamine (Example 3) was acetylated with acetic anhydride in dry pyridine at −10° C. The crude product was converted into the hydrochloric salt to obtain N-[4-[(1-azabicyclo[2.2.2]-oct-3-yl)oxy]phenyl]acetamide hydrochloride. M.p. >250° C.

EXAMPLE 5

In an analogous manner as described in Example 1 were prepared from (S)- or (R)-3-quinuclidinol:
(S)-3-(2-fluorophenoxy)-1-azabicyclo[2.2.2]octane ethanedioate. m.p. 158° C.; $[\alpha]_D^{20} = +27.5°$ (c=1, water).
(R)-3-(2-fluorophenoxy)-1-azabicyclo[2.2.2]octane ethanedioate. m.p. 159° C.; $[\alpha]_D^{20} = -27.5°$ (c=1, water).

EXAMPLE 6

In a analogous manner as described in Example 1, using 3-thioquinuclidinol (K. B. Shaw, Can. J. Chem., 43 (1965) 3112) instead of 3-quinuclidinol were prepared:
3-(2-nitrophenylthio)-1-azabicyclo[2.2.2]octane (Z)-2-butenedioate. m.p. 156° C.
3-[2-(trifluoromethyl)phenylthio]-1-azabicyclo[2.2.-2]octane (Z)-2-butenedioate. m.p. 120° C.
3-[4-(trifluoromethyl)phenylthio]-1-azabicyclo[2.2.-2]octane (Z)-2-butenedioate. m.p. 127° C.
2-[(1-azabicyclo[2.2.2]oct-3-yl)thio]benzenamine (Z)-2-butenedioate (obtained by iron/hydrochloric acid reduction of 3-(2-nitrophenylthio)-1-azabicyclo[2.2.-2]octane). m.p. 106° C.
N-[4-[(1-azabicyclo[2.2.2]oct-3-yl)thio]phenyl]acetamide (Z)-2-butenedioate.

We claim:
1. A 3-quinuclidine derivative comprising the formula I

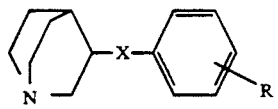

I wherein
X is S and R is one to five substituents independently selected from the group consisting of hydrogen, hydroxy, lower alkyl, lower alkoxy (wherein the alkyl group of said lower alkyl and lower alkoxy is a branched or unbranched alkyl group containing 1–4 carbons), lower aralkyloxy (wherein the alkyl group is a branched or unbranched alkyl group containing 1–4 carbons and the aryl moiety is a phenyl group optionally substituted with hydroxy, lower alkyl, lower alkoxy or halogen), lower alkanoyloxy, halogen, $NO_2$, $CF_3$, CN, $NR_1R_2$, and $COR_3$, in which $R_1$ and $R_2$ are independently selected from the group consisting of hydrogen, lower alkyl, and lower alkanoyl, and $R_3$ is selected from the group consisting of OH, lower alkyl, lower alkoxy and $NR_4R_5$, wherein $R_4$ and $R_5$ are independently hydrogen or lower alkyl;
or X is O and R is $CF_3$, bromine or iodine, or R is one substituent in the ortho position selected from the group of hydroxy, lower alkyl, lower alkoxy (wherein the alkyl group of said lower alkyl and lower alkoxy is a branched or unbranched alkyl group containing 1–4 carbons), lower aralkyloxy (wherein the alkyl group is a branched or unbranched alkyl group containing 1–4 carbons and the aryl moiety is a phenyl group optionally substituted with hydroxy, lower alkyl, lower alkoxy or halogen), lower alkanoyloxy, halogen, $NO_2$, $CF_3$, CN, $NR_1R_2$, and $COR_3$, in which $R_1$ and $R_2$ are independently selected from the group consisting of hydrogen, lower alkyl, and lower alkanoyl, and $R_3$ is selected from the group consisting of OH, lower alkyl, lower alkoxy and $NR_4R_5$, wherein $R_4$ and $R_5$ are independently hydrogen or lower alkyl;
or pharmaceutically acceptable salts thereof.

2. The 3-quinuclidine derivative of claim 1, wherein X is O.

3. The 3-quinuclidine derivative of claim 1, wherein when X is O or S, R is selected from the group consisting of $CF_3$, bromine and iodine.

4. The 3-quinuclidine derivative of claim 1, wherein R is a substituent in the ortho position.

5. A pharmaceutical composition comprising an effective amount of a 3-quinuclidine derivative comprising the formula I

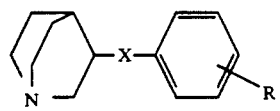

I wherein X is O or S, and R is one to five substituents independently selected from the group consisting of hydrogen, hydroxy, lower alkyl, lower alkoxy (wherein the alkyl group of said lower alkyl and lower alkoxy is a branched or unbranched alkyl group containing 1–4 carbons), lower aralkyloxy (wherein the alkyl group is a branched or unbranched alkyl group containing 1–4 carbons and the aryl moiety is a phenyl group optionally substituted with hydroxy, lower alkyl, lower alkoxy or halogen), lower alkanoyloxy, halogen, $NO_2$, $CF_3$, CN, $NR_1R_2$, and $COR_3$, in which $R_1$ and $R_2$ are independently selected from the group consisting of hydrogen, lower alkyl, and lower alkanoyl, and $R_3$ is selected from the group consisting of OH, lower alkyl, lower alkoxy and $NR_4R_5$, wherein $R_4$ and $R_5$ are independently hydrogen or lower alkyl; or pharmaceutically acceptable salts thereof for treating cholinergic deficiencies in humans in admixture with pharmaceutically acceptable auxiliaries.

6. A method of treating cholinergic deficiencies by administering therapeutically effective amounts of a 3-quinuclidine derivative comprising the formula I

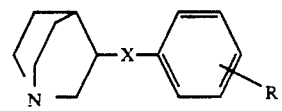

I wherein X is O or S, and R is one to five substituents independently selected from the group consisting of hydrogen, hydroxy, lower alkyl, lower alkoxy (wherein the alkyl group of said lower alkyl and lower alkoxy is a branched or unbranched alkyl group containing 1–4 carbons), lower aralkyloxy (wherein the alkyl group is a branched or unbranched alkyl group containing 1–4 carbons and the aryl moiety is a phenyl group optionally substituted with hydroxy, lower alkyl, lower alkoxy or halogen), lower alkanoyloxy, halogen, $NO_2$, $CF_3$, CN, $NR_1R_2$, and $COR_3$, in which $R_1$ and $R_2$ are independently selected from the group consisting of hydrogen, lower alkyl, and lower alkanoyl, and $R_3$ is selected from the group consisting of OH, lower alkyl, lower alkoxy and $NR_4R_5$, wherein $R_4$ and $R_5$ are independently hydrogen or lower alkyl; or pharmaceutically acceptable salts thereof to humans with said disorders and deficiencies.

7. The 3-quinuclidine derivative of claim 2, wherein R is selected from the group consisting of $CF_3$, bromine and iodine.

8. The 3-quinuclidine derivative of claim 2, wherein R is a substituent in the ortho position.

9. The 3-quinuclidine derivative of claim 3, wherein R is a substituent in the ortho position.

* * * * *